United States Patent
Claypool et al.

(10) Patent No.: US 7,892,240 B2
(45) Date of Patent: Feb. 22, 2011

(54) FEMORAL HEAD CENTER LOCATING APPARATUS AND METHOD

(75) Inventors: Jody L. Claypool, Columbia City, IN (US); Sudip Hui, Kolkata (IN); James S. Collins, Fort Wayne, IN (US); Donald M. Patmore, Warsaw, IN (US); Dale E. Walriven, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 818 days.

(21) Appl. No.: 11/854,740

(22) Filed: Sep. 13, 2007

(65) Prior Publication Data

US 2009/0076507 A1 Mar. 19, 2009

(51) Int. Cl.
*A61F 2/46* (2006.01)
*A61B 17/74* (2006.01)
*A61B 5/103* (2006.01)

(52) U.S. Cl. .............. 606/102; 606/86 R; 606/87; 606/88; 606/89; 600/595; 33/511; 33/512

(58) Field of Classification Search .......... 33/511–512; 600/102, 595; 606/53, 54, 102, 86 R, 87–89, 606/84, 85
See application file for complete search history.

(56) References Cited

U.S. PATENT DOCUMENTS 5,606,590 A 2/1997 Petersen et al.

*Primary Examiner*—Thomas C Barrett
*Assistant Examiner*—Sameh Boles
(74) *Attorney, Agent, or Firm*—Baker & Daniels LLP

(57) ABSTRACT

A femoral head center locating mechanism and method for using same. The femoral head center locating mechanism may include a frame and a plurality of lasers which emit laser beams which intersect to identify a reference point relative to a center of a femoral head.

7 Claims, 2 Drawing Sheets

FEMORAL HEAD CENTER LOCATING APPARATUS AND METHOD

BACKGROUND

1. Field of the Disclosure

The present disclosure relates to a femoral head center locating apparatus and method.

2. Description of the Related Art

A femur includes a femoral head which has a femoral head center. During an orthopaedic surgical procedure, a surgeon may need to identify the femoral head center to facilitate alignment of surgical instruments and positioning of orthopaedic implants, for example.

SUMMARY

The present disclosure provides a femoral head center locating mechanism and method for using same. The femoral head center locating mechanism may include a frame and a plurality of lasers which emit laser beams which intersect to identify a reference point relative to a center of a femoral head.

In one form thereof, the present disclosure provides a method for identifying a reference point relative to a femoral head center of a femur, including the steps of moving the femur along an arc of a circle to a first position; moving the femur along the arc of the circle to a second position; moving the femur along the arc of the circle to a third position; projecting a first light beam from a first midpoint between the first position and the second position; projecting a second light beam from a second midpoint between the second position and the third position; and identifying the reference point relative to the femoral head center by determining an intersection of the first light beam and the second light beam.

In another form thereof, the present disclosure provides an apparatus for identifying a reference point relative to a femoral head center of a femur, the apparatus including a frame including a first post; a second post; a third post; a first segment connecting the first post and the second post; and a second segment connecting the second post and the third post; and a first light emitting device positioned at a midpoint of the first segment; and a second light emitting device positioned at a midpoint of the second segment.

BRIEF DESCRIPTION OF THE DRAWINGS

The above-mentioned and other features of the disclosure, and the manner of attaining them, will become more apparent and will be better understood by reference to the following description of embodiments of the disclosure taken in conjunction with the accompanying drawings, wherein.

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

Figure 1:
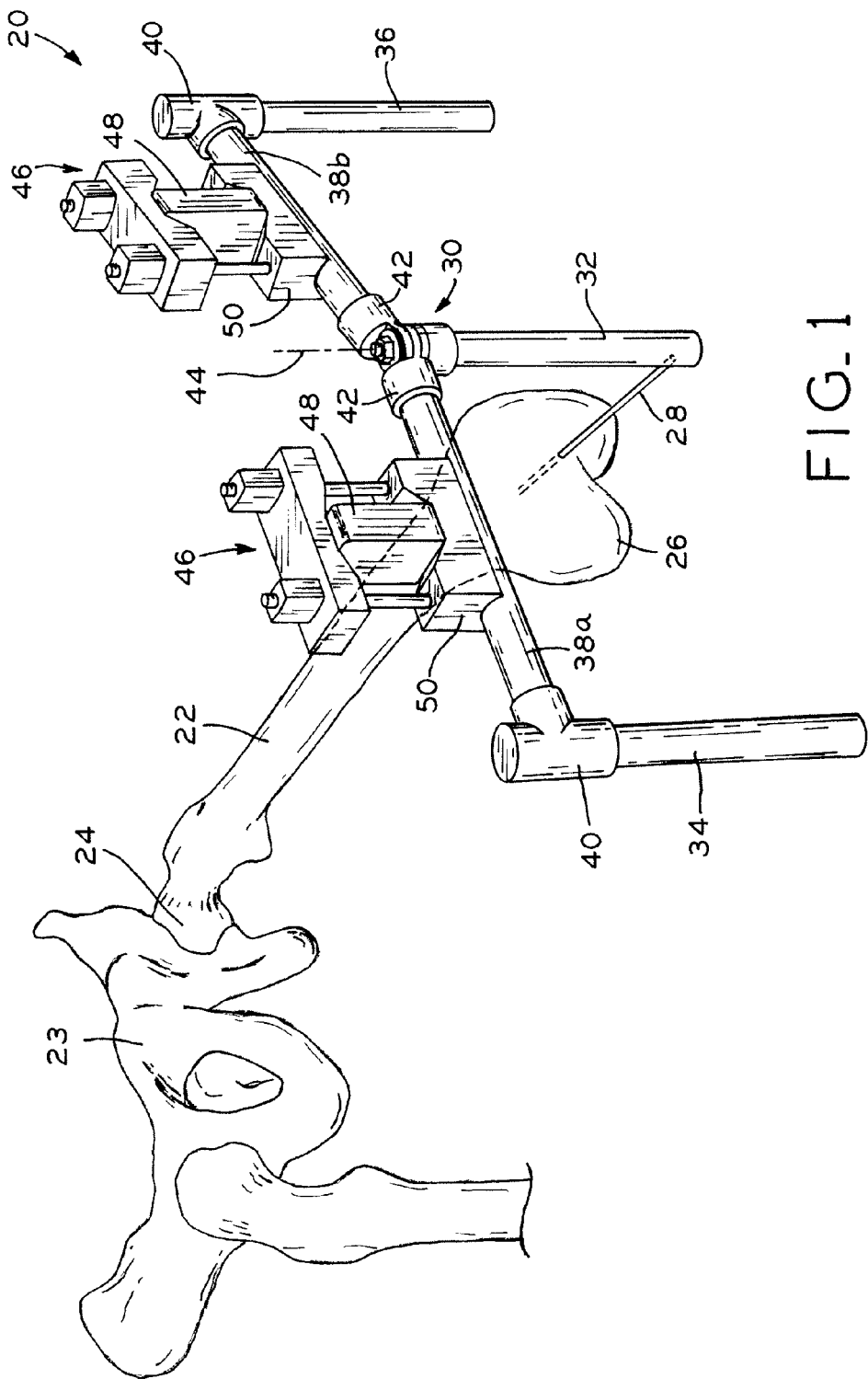
FIG. 1 is a perspective view of a femoral head center locating mechanism according to one embodiment of the present disclosure.

Referring now to FIG. 1, femoral head center locating mechanism 20 is shown and generally may include frame 30 and a plurality of light-emitting devices 46, such as laser devices, for example. Frame 30 may include posts 32, 34, 36, connecting links 38a, 38b, and connectors 40, 42. Each laser device 46 may include laser mount 50 and laser 48.

In an exemplary embodiment, post 32 is the central post of frame 30. Connectors 42 connect post 32 with connecting links 38a, 38b. One connector 40 connects connecting link 38a with post 34, thereby hingedly connecting post 32 with post 34, and another connector 40 connects connecting link 38b with post 36, thereby hingedly connecting post 32 with post 36. Post 32 defines rotational axis 44 about which connecting links 38a, 38b rotate relative to post 32. Posts 32, 34, 36 may be secured to a planar surface, such as a table, such that connecting links 38a, 38b lie parallel to the planar surface.

Laser devices 46 may be mounted to connecting links 38a, 38b in any suitable manner, such as via fasteners and/or an adhesive material, for example. In an exemplary embodiment, laser devices 46 are mounted such that each laser 48 is positioned at a midpoint of each respective connecting link 38a, 38b. Moreover, each laser 48 is oriented such that laser beams 52a, 52b (FIGS. 2-4) are projected in directions substantially perpendicular to a longitudinal axis of each connecting link 38a, 38b, respectively.

Femoral head center locating mechanism 20 may be used to define a reference point on a line on which femoral head center 54 (FIG. 4) of femoral head 24 of femur 22 is located. Femur 22 may be rotated in a single plane through a range of motion which generally defines an arc of a circle. Femoral head center 54 (FIG. 4) is defined at the center of the circle defined by the rotation of femur 22. In operation, a surgeon or other user of femoral head center locating mechanism 20 securely attaches rod 28 or other suitable structure to distal end 26 of femur 22. Rod 28 may be screwed, driven, or otherwise inserted into distal end 26 to securely attach rod 28 to femur 22. Rod 28 may be removed after a surgical procedure. In an alternative embodiment, rod 28 is eliminated and a user may use femoral head center locating mechanism 20 with femur 22 without any additional structure attached thereto.

Figures 2, 3, 4:
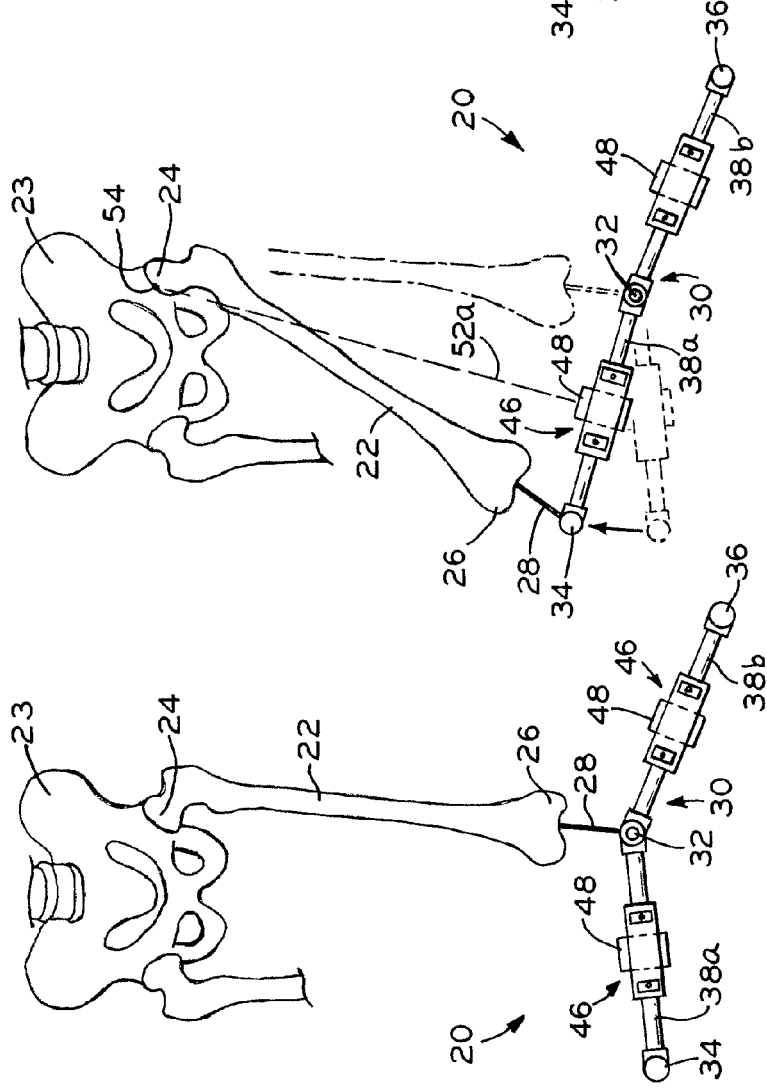
FIG. 2 is a plan view of the mechanism of FIG. 1, illustrating one step of a method using the femoral head center locating mechanism of FIG. 1.
FIG. 3 is a plan view of the mechanism of FIG. 1, illustrating another step of a method using the femoral head center locating mechanism of FIG. 1.
FIG. 4 is a plan view of the mechanism of FIG. 1, illustrating yet another step of a method using the femoral head center locating mechanism of FIG. 1.

As shown in FIG. 2, once rod 28 is secured to femur 22, femur 22 is moved to a first location such that rod 28 contacts post 32 at a first position. Rod 28 may be positioned such that rod 28 contacts either a top end or a bottom end of post 32 or any designated location on post 32. Post 32 thereby defines a first point on the arc of the circle defined by the rotation of femur 22. Throughout the following steps of the procedure, post 32 remains stationary.

As shown in FIG. 3, femur 22 is then moved to a second location such that rod 28 contacts post 34 at a second position. Rod 28 must be positioned relative to post 34 in the same manner as rod 28 was positioned relative to post 32, i.e., after contacting post 32 at the first position, rod 28 must be moved in a plane which is perpendicular to posts 32, 34, 36 and which contains the first position defined as the point of contact between post 32 and rod 28. Rod 28 must contact post 34 at a location on post 34 coincident with this perpendicular plane such that the points of contact between rod 28 and post 32 and between rod 28 and post 34 both lie in this plane. Post 34 may be rotated relative to post 32 via rotation about rotation axis 44 of post 32 such that rod 28 may be positioned in this manner. Post 34 thereby defines a second point on the arc of the circle defined by the rotation of femur 22 and connecting link 38a, which connects post 34 and post 32, corresponds to a first chord of the arc.

As shown in FIG. 4, femur 22 is then moved to a third location such that rod 28 contacts post 36 at a third position. Rod 28 again must be positioned relative to post 36 in the same manner as rod 28 was positioned relative to posts 32, 34, i.e., after contacting posts 32, 34, rod 28 must be moved in the perpendicular plane described above. Rod 28 must contact post 36 at a location on post 36 coincident with this perpendicular plane such that the points of contact between rod 28 and post 32, between rod 28 and post 34, and between rod 28 and post 36 all lie in the plane. Post 36 may be rotated relative to post 32 via rotation about rotation axis 44 of post 32 such that rod 28 may be positioned in this manner. Post 36 thereby defines a third point on the arc of the circle defined by the rotation of femur 22 and connecting link 38b, which connects post 36 and post 32, corresponds to a second chord of the arc. Thus, the arc of the circle defined by the rotation of femur 22 lies in the perpendicular plane described above and connecting links 38a, 38b correspond to chords of the arc and lie parallel to the perpendicular plane.

Referring again to FIG. 4, posts 32, 34, 36 correspond to three points on the arc of the circle defined by the rotation of femur 22 and connecting links 38a, 38b correspond to two chords of the circle. Laser 48 positioned on connecting link 38a projects laser beam 52a in a general direction toward femoral head 24 and laser 48 positioned on connecting link 38b projects laser beam 52b in a general direction toward femoral head 24. Laser beam 52a defines a perpendicular bisecting line relative to the first chord corresponding to connecting link 38a of the arc of the circle defined by the rotation of femur 22; therefore, laser beam 52a perpendicularly intersects a line extending through femoral head center 54. Laser beam 52b defines a perpendicular bisecting line relative to the second chord defined by connecting link 38b of the arc of the circle defined by the rotation of femur 22; therefore, laser beam 52b perpendicularly intersects a line extending through femoral head center 54. The intersection of laser beam 52a and laser beam 52b thereby identifies a reference point on a line which extends perpendicular to both laser beam 52a and laser beam 52b and which extends through femoral head center 54 of femoral head 24, i.e., the location of the center of the circle defined by the rotation of femur 22.

The line which extends through femoral head center 54 and which is perpendicular to both laser beams 52a, 52b, may be used in a method for identifying a mechanical axis of femur 22. For example, a user may identify a point in the intercondylar notch of distal end 26 of femur 22. A line drawn through this intercondylar notch point and extending perpendicularly through and intersecting the line extending through the femoral head center 54 and perpendicular to both laser beams 52a, 52b may define the mechanical axis of femur 22.

Although described throughout as including laser 48 and laser beam 52, device 46 may be based on any other light-emitting system or a physical structure such as a rod extending from device 46. For example, device 46 may include a light-emitting device which produces a narrow and/or coherent light beam similar to beam 52 such that an intersection point between two light beams is easily identified. One such light-emitting device may be a light-emitting diode which produces a narrow, coherent light beam similar to a laser beam. In one embodiment, a background may be provided near the intersection of laser beams 52a, 52b to facilitate visualizing the intersection of laser beams 52a, 52b.

Although described above as post 32 defining a first location, post 34 defining a second location, and post 36 defining a third location, posts 32, 34, 36 could be positioned such that post 34 was the first location, post 32 was the second location, and post 36 was the third location, or posts 32, 34, 36 could be positioned such that post 36 was the first location, post 32 was the second location, and post 34 was the third location, or posts 32, 34, 36 could be positioned such that post 32 was the first location, post 36 was the second location, and post 34 was the third location.

Although described throughout as attached to distal end 26 of femur 22, rod 28 or other suitable structure 28 could be attached at any point on femur 22. Alternatively, no structure 28 may be attached to femur 22 and, instead, a distal most point on distal end 26 may be used to contact each post 32, 34, 36 in the same manner as described above with reference to rod 28.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method for identifying a reference point relative to a femoral head center of a femur having a femoral head, comprising the steps of:
    moving the femur along an arc of a circle to a first position;
    moving the femur along the arc of the circle to a second position;
    moving the femur along the arc of the circle to a third position;
    projecting a first light beam in a general direction toward the femoral head from a first midpoint between the first position and the second position;
    projecting a second light beam in a general direction toward the femoral head from a second midpoint between the second position and the third position; and
    identifying the reference point relative to the femoral head center by determining an intersection of the first light beam and the second light beam.

2. The method of claim 1, wherein the first position and the second position define a first chord of the circle, said first projecting step comprising projecting the first light beam in a direction substantially perpendicular to the first chord.

3. The method of claim 2, wherein said first projecting step further comprises projecting the first light beam in a direction which substantially bisects the first chord.

4. The method of claim 1, wherein the second position and the third position define a second chord of the circle, said second projecting step comprising projecting the second light beam in a direction substantially perpendicular to the second chord.

5. The method of claim 4, wherein said second projecting step further comprises projecting the second light beam in a direction which substantially bisects the second chord.

6. The method of claim 1, further comprising the step of providing a frame having a first post corresponding to the first position, a second post corresponding to the second position, and a third post corresponding to the third position, wherein the first, second, and third posts are arranged parallel to each other, wherein the first position, the second position, and the third position lie in a plane extending perpendicular to each of the first, second, and third posts.

7. The method of claim 1, further comprising the step of providing a line extending through the reference point and extending perpendicular to the first light beam and the second light beam, the line extending through the femoral head center.

* * * * *